United States Patent [19]
Bryant et al.

[11] Patent Number: 5,990,129
[45] Date of Patent: Nov. 23, 1999

[54] METHODS FOR REGULATING TRKA EXPRESSION

[75] Inventors: Henry Uhlman Bryant, Indianapolis; Robert Frank Santerre, Zionsville, both of Ind.

[73] Assignee: Eli Lilly and Company, Indianapolis, Ind.

[21] Appl. No.: 09/150,271

[22] Filed: Sep. 9, 1998

Related U.S. Application Data

[60] Provisional application No. 60/059,617, Sep. 23, 1997.
[51] Int. Cl.[6] .................. A61K 31/445; A61K 31/40; A61K 31/38
[52] U.S. Cl. .................... 514/324; 514/422; 514/443
[58] Field of Search ................... 514/324, 422, 514/443

[56] References Cited

U.S. PATENT DOCUMENTS

| | | |
|---|---|---|
| 4,133,814 | 1/1979 | Jones et al. . |
| 4,380,635 | 4/1983 | Peters . |
| 4,418,068 | 11/1983 | Jones . |
| 5,075,321 | 12/1991 | Schreiber . |
| 5,434,166 | 7/1995 | Glasebrook . |
| 5,441,947 | 8/1995 | Dodge et al. . |
| 5,445,941 | 8/1995 | Yang . |
| 5,482,927 | 1/1996 | Maniar et al. . |
| 5,482,949 | 1/1996 | Black et al. . |
| 5,494,929 | 2/1996 | Grese ....................... 514/443 |
| 5,504,094 | 4/1996 | Bruns, Jr. et al. . |
| 5,512,296 | 4/1996 | Cullinan . |
| 5,545,647 | 8/1996 | Tanaka et al. . |
| 5,686,476 | 11/1997 | May . |

FOREIGN PATENT DOCUMENTS

| | | |
|---|---|---|
| 0 659 413 A3 | 12/1994 | European Pat. Off. . |
| 0 729 754 | 2/1996 | European Pat. Off. . |
| 0 747 052 | 5/1996 | European Pat. Off. . |
| 074 747 051 | 5/1996 | European Pat. Off. . |
| WO93/10113 | 5/1993 | Japan . |
| WO93/10741 | 6/1993 | WIPO . |
| WO96/40137 | 6/1995 | WIPO . |
| WO996/40130 | 6/1995 | WIPO . |

OTHER PUBLICATIONS

Draper et al., "Effects of Raloxifene (LY139481 HC1) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti–estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti–Estrogen, Simulates the Effects of Estrogen in Inhibiting Bone Resorption Through Regulating TGFB–3 Expression in Bone;".Am Soc. for Bone and Min. Res., Tampa, Sep. 18–22, 1993.
Black et al., "Distinct, Structure–Related Profiles of Estrogenic and Anti–Estrogenic Activity in the Tamoxifen and LY117018 Series;" The Endocrine Society, Abstract 1982.
Black et al. "Uterine Bioassay of Tamoxifen, and New Estrogen Antagonist (LY117018) in Rats and Mice," Life Sciences, 26:1980, 1453–1458, 1980.
Black et al., "Differential Interaction of Antiestrogens with Cytosol Estrogen Receptors," Molecular and Cellular Endocrinology, 22:1981, 95–103, 1981.

(List continued on next page.)

Primary Examiner—William R. A. Jarvis
Attorney, Agent, or Firm—William R. Boudreaux; James J. Sales

[57] ABSTRACT

The current invention provides methods for the up-regulation of trkA in a mammal, including humans, comprising the administration of an effective amount of a compound of formula I

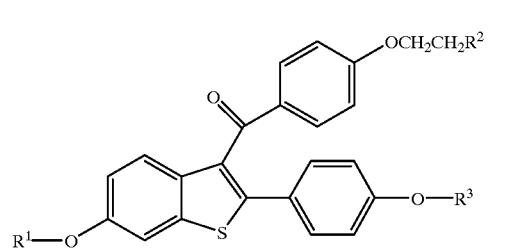

wherein $R^1$ and $R^3$ are, independently, —H, —$CH_3$, —CO($C_1$–$C_6$ alkyl), or —COAr, where Ar is optionally substituted phenyl;

$R^2$ is selected from the group consisting of pyrrolidine, piperidine, and hexamethyleneimino; or a pharmaceutically acceptable salt or solvate thereof.

In addition, the current invention provides method to increase the effect of NGF (Nerve Growth Factor), NGF-like activities or NGF agonists, whether such is from endogenous or exogenous sources.

Further, the current invention provides methods for maintaining the homeostasis and health of the hippocampus, hypothalamus, and cortex, thus maintaining their biological functions.

6 Claims, No Drawings

OTHER PUBLICATIONS

Black et al., "Evidence for Biological Action of the Antiestrogens LY1107018 and Tamoxifen by Different Mechanisms," Endocrinology 109;1981, 987–989, 1981.

Black, L.J. "Biological Actions and Binding Properites of a New Estrogen Antagosist LY117018," In: Homone Antagonists, 129–82, 1982 (M.K. Agarwal ed.).

Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32, 1983, 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2(4–methoxyphenyl)–1–napthalenyl] [4–[2–pyrrolidinyl)ethoxyl]–phenyl] methanone, methanesulfonic acid salt, Journal of Medicinal Chemistry 22, 1979, 962–966.

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl]methanone Hydrochloride (LY156758), a Remarkably Effective Estrogen Antagonist with Only Minimal Intrinsic Estrogenicity, J. Med. Chem. 27(8), 1984, 1057–1066.

Metzger, et al. Estrogen Receptor Blockade with Tamoxifen Diminishes Growth Hormone Secretion in Boys: Evidence for a Stimulatory Role of Endogenous Estrogens during Male Adolescence Journal of Clinical Endocrinology and Metabolism, vol. 79(2), 1994, 513–518.

Weissberger, et al., Activation of the Somatotropic Axis by Testosterone in Adult Males: Evidence for the Role of Aromatization, Journal of Clinical Endocrinology and Metabolism, vol. 76(6), 1407–1412, 1993.

Metzger, et al., Androgen Receptor Blockade with Flutamide Enhances Growth Hormone Secretion in Late Pubertal Males: Evidence for Independent Actions of Estrogen and Androgen, Journal of Clinical Endocrinology and Metabolism, vol. 76(5), 1993, 1147–1152.

Evans, et al., Effects of Sex and Age on the 24–Hour Profile of Growth Hormone Secretion in Man: Importance of Endogenous Estradiol Concentrations,Journal of Clinical Endocrinology and Metabolism, vol. 64(1) 1987.

Spijkstra, et al., Divergent Effects of the Antiestrogen Tamoxifen and of Estrogens on Luteinzing Hormone (LH) Pulse Frequency, But Not on Basal LH Levels and LH Pulse Amplitude in Men,, Journal of Clinical Endocrinology and Metabolism, vol. 64(1), 1987.

Caruso–Nicoletti, et al., Short Term, Low Dose Estradiol Accelerates Ulnar Growth in Boys, J. Clin. Endocrinol. Metabolism, vol. 61(5), 1985.

Database US Patfull on STN, No. 96:36299, Cullinan et al., of the abstract to U.S. Patent No. 5,512,296, Issued on Apr. 20, 1995.

Miranda et al, Chemical Abstracts, vol. 122, abstract No. 205433, 1994.

Frolik et al, Chemical Abstracts, vol. 125, abstract No. 185773, 1996.

METHODS FOR REGULATING TRKA EXPRESSION

This Application claims the benefit of U.S. Provisional Application No. 60/059,617, filed Sep. 23, 1997.

FIELD OF THE INVENTION

The current invention deals with the areas of medicinal chemistry, molecular biology, and pharmacology related to the regulation of trkA, the receptor for the neurotrophin Nerve Growth Factor (NGF), by the administration of 2-aryl-3-aroylbenzo[b] thiophenes.

BACKGROUND OF THE INVENTION

The trk proteins are a family of receptor tyrosine kinases, whose function is the signal transduction of neurotrophins. The trk receptor family consists of three known members (A–C), each binding specific neurotrophins. Thus, the neurotrophins induce many of their effects through one of these trk receptors. Most germane to the current invention is the trkA receptor, which binds the neurotrophin Nerve Growth Factor (NGF).

NGF is an essential neurotrophin in maintaining homeostasis of nerve tissue in both the peripheral and central nervous system. The critical activity of NGF has been demonstrated in the development, maintenance, and repair of nerves. In addition to the homeostatic benefit of endogenous NGF, it has been suggested that exogenously administered NGF, molecules having NGF-agonist activity or molecules that can stimulate NGF or NGF-like activity, may be useful in treating damaged nerve tissue, e.g., nerve damage due to trauma, surgery, disease, old age, etc. It would be useful if an agent were available which would enhance the beneficial effects of endogenous or exogenous NGF, NGF-like activities or NGF agonists. Such an agent might be one which would increase the response of nerves to NGF via up-regulating the molecular target of NGF, i.e., its receptor, trkA. For further information, see: "Severe Sensory and Sympathetic Neuropathies in Mice Carrying a Disrupted trk/NGF Receptor Gene", Smeyne, R. J., et al., Nature, 368, pp. 246–248, Mar. 17, 1994.

Recently, it has been shown that the hormone estrogen regulates the gene coding the NGF receptor, viz., trkA. It has been known that estrogen appears to have a beneficial effect on maintaining healthy nerve tissue in many animal species, including humans. For further information, see: "Estrogen Differentially Regulates Estrogen and Nerve Growth Factor Receptor mRNAs in Adult Sensory Neurons", Sohrabji, F., et al., J. Neurosci., 14(2), pp.459–471 (1994) and "The Effects of Ovariectomy and Estrogen Replacement on trkA and Choline Acetyltransferase mRNA Expression in the Basal Forebrain of the Adult Female Sprague-Dawley Rat", McMillan, P. J., et al., J. Neurosci., 16(5), pp. 1860–1865, 1996 and references cited therein.

Therefore, it would seem reasonable that estrogens, e.g., 17-β-estradiol, estrone, and the like, would be useful in the treatment of conditions where increasing the effect of molecules that directly or indirectly activate trkA receptor would be beneficial. However, estrogens are known to have many detrimental side-effects, e.g., cancer risk, uterine stimulation, and the like, vitiating their use in such cases.

It would be beneficial if an agent were available that would up-regulate the trkA/NGF system without estrogenic side-effects.

SUMMARY OF THE INVENTION

The current invention provides methods for the up-regulation of trkA in a mammal, including humans, comprising the administration of an effective amount of a compound of formula I

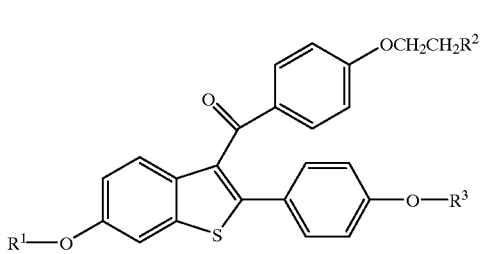

wherein $R^1$ and $R^3$ are, independently, —H, —CH$_3$, —CO (C$_1$–C$_6$ alkyl), or —COAr, where Ar is optionally substituted phenyl;

$R^2$ is selected from the group consisting of pyrrolidine, piperidine, and hexamethyleneimino; or a pharmaceutically acceptable salt or solvate thereof.

In addition, the current invention provides methods to increase the effect of NGF (Nerve Growth Factor), NGF-like activities or NGF agonists whether provided from endogenous of exogenous sources.

Further, the current invention provides methods for maintaining the homeostasis and health of the hippocampus, hypothalamus, and cortex, thus maintaining their biological functions.

DETAILED DESCRIPTION OF THE INVENTION

The current invention is related to the discovery that a select group of 2-aryl-aroylbenzo[b] thiophenes i.e., the compounds of formula I, are useful for up-regulating trkA, and other methods of the current invention.

General terms used in the description of compounds herein described bear their usual meanings. For example, "C$_1$–C$_6$ alkyl" refers to straight or branched aliphatic chains of 1 to 6 carbon atoms including methyl, ethyl, propyl, iso-propyl, n-butyl, pentyl, hexyl and the like.

The term "substituted phenyl" refers to a phenyl group alone or having one or more substituents selected from the group consisting of C$_1$–C$_4$ alkyl, C$_1$–C$_4$ alkoxy, hydroxy, nitro, chloro, fluoro, or tri (chloro or fluoro)methyl. "OC$_1$–C$_4$ alkyl" refers a C$_1$–C$_4$ alkyl group attached through an oxygen bridge such as methoxy, ethoxy, n-propoxy, iso-propoxy, and the like.

The term "pharmaceutically acceptable salt" refers to either acid or base addition salts which are known to be non-toxic and are commonly used in the pharmaceutical literature. Commonly used acid addition salts are inorganic salts formed by the addition of sulfuric acid, nitric acid, hydrochloric acid, hydrobromic acid phosphoric acid, phosphorous acid and the like; or organic salts formed by the addition of acetic acid, formic acid, benzoic acid, citric acid, methanesulfonic acid and the like. Commonly used basic addition salts are the salts formed by alkali or alkaline earth hydroxides, ammonium hydroxide, alkyl or aromatic amines and the like. A preferred salt of this invention is the hydrochloride salt.

The term "solvate" refers to a molecular complex of a compound of formula I with one or more solvent molecules. Such solvent molecules would be those commonly used in the pharmaceutical literature, which are known to be innocuous to the recipient, e.g., water, ethanol, and the like.

The compounds of this invention are derivatives of centrally located carbon, i.e., the "—CO—" moiety in formula I, thus derivatives are methanones, e.g., a compound of A—CO—B, would be named [A][B]methanone. Further the compounds of formula I are derivatives of benzo[b] thiophene which is named and numbered according to the Ring Index, The American Chemical Society, as follows:

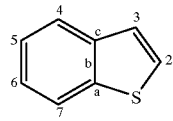

Thus, Raloxifene hydrochloride, which is a preferred embodiment of this invention, is a compound of formula I, where $R^1$ and $R^3$ are hydrogen; $R^2$ is N-piperidinyl; and it is as its hydrochloride salt. Raloxifene hydrochloride is named: [2-(4-hydroxyphenyl)-6-hydroxybenzo[b]thie-3-yl][4-[2-(1-piperidenyl)ethoxy]phenyl]methanone hydrochloride.

All of the compounds used in the methods and formulations of the current invention can be made according to procedures, such as those detailed in U.S. Pat. No. 4,133,814 and U.S. Pat. No. 4,418,068, each of which is included by reference, herein. In general, the process starts with a benzo[b]thiophene having a 6-hydroxyl group and a 2-(4-hydroxylphenyl) group. The starting compound is protected, alkylated, and de-protected to form the compounds of formula I. The formula I compounds which are carboxylic esters may be prepared by methods described in U.S. Pat. No. 5,393,763, which is included by reference, herein.

The compounds of formula I are members of a group of compounds known as "anti-estrogen" which have selective estrogenic agonist and antagonist pharmacologic activities. For example, formula I compounds act as estrogen agonists in treating pathologic sequelae caused by the cessation of menses in females (see: Draper et al., "Effects of Raloxifene (LY139481 HCl) on Biochemical Markers of Bone and Lipid Metabolism in Healthy Postmenopausal Women", Hong Kong, Fourth Int'l. Symp. on Osteoporosis, Mar. 29, 1993.; U.S. Pat. Nos. 5,393,763, 5,464,845, and 5,391,557). In addition, the compounds of formula I have been shown to have the potential to protect CNS nerve tissue by inhibiting the damaging effects initiated by the causal condition, hypoglycemia, (U.S. Pat. No. 5,512,296), and to help correct inappropriate and imperfect tissue repair (U.S. Pat. No. 5,574,047).

As used herein, the term "effective amount" means an amount of compound of the present invention which is capable of up-regulating the trkA receptor in neurons, thereby increasing the pharmacologic action of NGF, NGF-like activities or NGF agonists and maintaining the healthy homeostasis of nerve tissue.

Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethyl glycols. Final pharmaceutical forms include pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to up-regulate the trkA receptor according to this invention will depend upon the particular circumstances of the conditions to be treated. Such considerations as dosage, route of administration, and frequency of dosing are best decided by the attending physician. Generally, accepted and effective doses for oral or parentral administration will be from 10 mg to 800 mg, and more typically between 20 mg and 100 mg, expressed as equivalents of the free base of a compound of formula I. Such dosages will be administered to a patient in need of treatment from once to three times each day or as often as needed to effectively up-regulate the trkA receptor. A preferred amount is 60 mg of Raloxifene hydrochloride (56 mg of free base) per day via an oral route of administration.

The formulations which follow are given for purposes of illustration and are not intended to be limiting in any way. The total active ingredients in such formulations comprises from 0.1% to 99.9% by weight of the formulation. The term "active ingredient" means a compound of formula I, preferably Raloxifene hydrochloride.

| Formulation 1: Gelatin Capsules | |
|---|---|
| Ingredient | Quantity (mg/capsule) |
| Active Ingredient | 50–600 |
| Starch NF | 0–500 |
| Starch flowable powder | 0–500 |
| Silicone fluid 350 centistrokes | 0–15 |

The ingredients are blended, passed through a No. 45 mesh U.S. sieve, and filled into hard gelatin capsules.

| Formulation 2: Tablets | |
|---|---|
| Ingredient | Quantity (mg/tablet) |
| Active Ingredient | 50–600 |
| Starch | 10–50 |
| Cellulose, microcrystalline | 10–20 |
| Polyvinylpyrrolidone (as 10% solution in water) | 5 |
| Sodium carboxymethyl cellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–600° C. and passed through a No. 18 mesh U.S. sieve. The sodium carboxymethyl cellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
| --- | --- |
| Active Ingredient | 0.50 |
| Ethanol | 29.50 |
| Propellant 22 | 70.00 |
| (Chlorodifluoromethane) | |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suspension

Suspensions each containing 100 mg of a compound of formula I per 5 mL dose.

| Ingredient | Weight |
| --- | --- |
| Active Ingredient | 100 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and the mixture is stirred thoroughly. Additional water is added to bring the entire mixture to the required volume.

Assay

The following demonstration of the methods of the current invention are presented for the purposes of illustration and are not intended to limit the scope of this invention in any way.

Forty female Sprague Dawley rats (weight range of 200 to 225 g, seventy-five days old) are obtained from Charles River Laboratories (Portage, Mich.). The animals are either bilaterally ovariectomized (OVX) or exposed to a sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

The animals are dosed daily by oral gavage with either compound 1, [2-(4-hydroxyphenyl)-6-hydroxybenzo[b]thien-3-yl][4-[2-(1-pyrolidinyl)ethoxy]phenyl]methanone hydrochloride, at 3 mg/kg, or with a placebo vehicle containing 10% cyclodextrin. There are twenty animals per each dosing regimen. Groups of four animals are taken off study at time periods of 0.5, 3, 12, 24, and 48 hours. The animals are sacrificed and brains dissected, the particular portions of the brains are pooled, homogenized, and RNA extracted. Twenty microgram samples of the pooled RNAs are applied to a gel and separated on a gel with electrophoresis and blotted to Hybond membranes for a Northern Analysis. The samples are analyzed by hybridization with a $^{33}$P-labeled PCR fragment probe to either trkA or 18S rRNA. The samples are quantitated by exposure to a phosphorimager screen and the data processed by ImageQuant software. The 18S rRNA blots are a normalizing control, thus increases in trkA mRNA expression are in relation to the 18S rRNA level.

The results of this demonstration are given in Table 1 and increases in trkA mRNA expression are increases between drug treated and placebo animals.

TABLE 1

| Brain Section | trkA mRNA Change in Treated Animals |
| --- | --- |
| Hippocampus | 2× Increase @ 24 hours |
| Hypothalamus | 3× Increase @ 24 hours |
| Cerebellum | No change |
| Cortex | 2× Increase @ 48 hours |

The receptor, trkA, and NGF are found not only in the CNS, but also in the peripheral nerves. NGF and the other neurotrophins exhibit much the same activity in the peripheral nerves as they do in the CNS. Thus, compounds of the current invention would have the same beneficial effect in peripheral nerves, i.e., enhancement of the effect of NGF, NGF-like activities or NGF agonists, as they would in the CNS.

Compounds of the current invention may be used both in treatment and prophylactic modalities. For example, in a treatment modality, patients suffering from a neurodegenerative disease or trauma where neurons have suffered damage and are attempting to regenerate aided by the action of either endogenous or exogenous NGF, NGF-like activities or NGF agonists may be benefited. Particular circumstances illustrating a treatment modality include, but are not limited to neuronal healing and regeneration after cerebrovascular events, e.g., ischemic stroke, arterial occlusions, arterial insufficiency, embolism, aneurysm rupture, hemorrhage, and the like; trauma due to accident or surgery to either the CNS or peripheral nerves; or infection; inflammation; hypertension of cranial pressure; etc.

As mentioned, supra, the methods of the current invention would enhance the beneficial action of both endogenous and exogenous NGF, NGF-like activities or NGF agonists. Enhancement of the beneficial action of endogenous NGF or NGF-like activities would be in treatment of those conditions where the natural healing process is being allowed to proceed without external addition of NGF, e.g., a normal recovery from meningitis, encephalitis, an ischemic event, or the like. Enhancement of the beneficial action of exogenous NGF or NGF agonists would be in treatment of those conditions where the healing process is being accelerated with external addition of NGF or NGF agonists, e.g., administering such at the site of a surgical procedure, ischemic site, trauma, or the like.

The methods of the current invention when used in a prophylactic mode to enhance the beneficial action of endogenous NGF or NGF-like activities to prevent the pathogenic sequelae which would result from any condition or disease before such sequelae are manifested. Additionally, the methods of the current invention are useful for ameliorating the neuro-degenerative effects of aging. Thus, the current invention maintains good neuronal health.

This maintenance of good neuronal health is especially beneficial to the CNS and, in particular, the hippocampus, hypothalamic, and the cortex regions of the brain. Not only are the methods of the current invention especially beneficial to the particular portions of the brain, but also would be especially useful in maintaining the neurological functions of those portions, e.g., cognitive functions associated with the cortex, sensory perception associated with the hippocampus, etc.

We claim:

1. A method of up-regulating the expression of trkA in nerve tissue in a human comprising the administration to a human in need thereof an effective amount of a compound of formula I

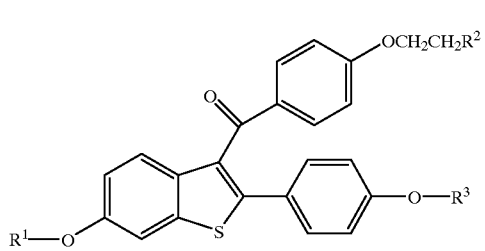

wherein $R^1$ and $R^3$ are, independently, —H, —CH$_3$, —CO (C$_1$–C$_6$ alkyl), or —COAr, where Ar is optionally substituted phenyl, $R^2$ is selected from the group consisting of pyrrolidine, piperidine, and hexamethyleneimino; or a pharmaceutically acceptable salt or solvate thereof.

2. A method according to claim 1 wherein is $R^1$ and $R^3$ are hydrogen, $R^2$ is N-piperidinyl, and the hydrochloride salt thereof.

3. A method according to claim 1 wherein is $R^1$ and $R^3$ are hydrogen, $R^2$ is N-pyrolidinyl, and the hydrochloride salt thereof.

4. A method according to claim 1 wherein the nerve tissue is in the central nervous system (CNS).

5. A method according to claim 4 wherein the CNS tissue is located in the hippocampal, hypothalamic, or the cortical regions of the brain.

6. A method of enchancing the neuroregenerative and/or neuroprotective effects of the neurotrophin nerve growth factor (NGF), NGF-like activities or NGF agonist activities in a human, comprising administering to a human in need thereof a compound of formula I

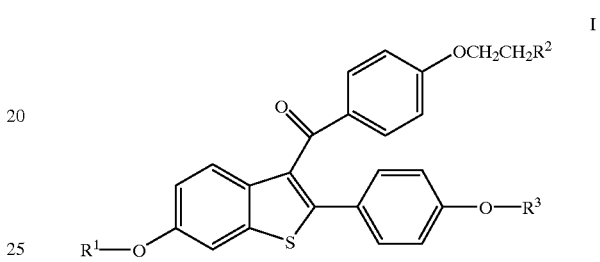

wherein $R^1$ and $R^3$ are, independently, —H, —CH$_3$, —CO (C$_1$–C$_6$ alkyl), or —COAr, where Ar is optionally substituted phenyl;

$R^2$ is selected from the group consisting of pyrrolidine, piperidine, and hexamethyleneimino; or a pharmaceutically acceptable salt or solvate thereof.

* * * * *